United States Patent
Pak

(10) Patent No.: US 7,507,844 B2
(45) Date of Patent: Mar. 24, 2009

(54) NANOMETER SCALE RESTRUCTURING OF ALUMINA CARRIER SURFACE AND CATALYSTS FOR THE PRODUCTION OF ALKENE OXIDES

(75) Inventor: Serguei Pak, Teaneck, NJ (US)

(73) Assignee: SD Lizenzverwertungsgesellschaft mbH & Co. KG, Munich (DE)

(*) Notice: Subject to any disclaimer, the term of this patent is extended or adjusted under 35 U.S.C. 154(b) by 342 days.

(21) Appl. No.: 11/124,645

(22) Filed: May 9, 2005

(65) Prior Publication Data
US 2006/0252643 A1   Nov. 9, 2006

(51) Int. Cl.
C07D 301/10   (2006.01)
B01J 23/00   (2006.01)
B01J 29/00   (2006.01)
B01J 21/00   (2006.01)
B01J 20/00   (2006.01)

(52) U.S. Cl. .......................... 549/534; 502/63; 502/64; 502/78; 502/80; 502/84; 502/87; 502/180; 502/181; 502/182; 502/183; 502/184; 502/185; 502/347; 502/348; 502/349; 502/350; 502/351; 502/355; 502/415; 502/439; 502/527.19; 502/527.24; 502/340; 502/341

(58) Field of Classification Search .................. 502/63, 502/64, 80, 84, 87, 178, 180, 185, 240, 300, 502/349–351, 355, 415, 439, 527.19, 527.24, 502/181, 182, 183, 184, 347, 348, 340, 341, 502/78; 549/523, 534
See application file for complete search history.

(56) References Cited

U.S. PATENT DOCUMENTS

| | | | |
|---|---|---|---|
| 3,518,206 A | 6/1970 | Sowards et al. | |
| 3,628,914 A | 12/1971 | Graulier | 23/143 |
| 3,966,646 A | 6/1976 | Noakes et al. | |
| 3,997,476 A | 12/1976 | Cull | 252/463 |
| 4,749,671 A * | 6/1988 | Saito et al. | 502/64 |
| 4,803,189 A | 2/1989 | Swars | |
| 5,102,848 A | 4/1992 | Soo et al. | 502/218 |
| 5,380,697 A * | 1/1995 | Matusz et al. | 502/348 |
| 5,629,258 A | 5/1997 | Suess et al. | |
| 5,923,408 A * | 7/1999 | Takabayashi | 355/53 |
| 6,143,057 A | 11/2000 | Bulow et al. | |
| 6,147,027 A | 11/2000 | Miyake et al. | |
| 6,267,932 B1 | 7/2001 | Nilsson | |
| 6,288,008 B1 | 9/2001 | Matsumoto | |
| 6,299,429 B1 * | 10/2001 | Xuan | 425/174.4 |
| 6,750,173 B2 | 6/2004 | Rizkalla et al. | |
| 6,762,311 B2 * | 7/2004 | Rizkalla et al. | 549/534 |
| 6,831,037 B2 * | 12/2004 | Szymanski et al. | 502/355 |
| 6,846,774 B2 | 1/2005 | Rizkalla | 502/348 |
| 7,202,418 B2 * | 4/2007 | Glew | 174/113 C |
| 2003/0100446 A1 * | 5/2003 | Hase et al. | 502/302 |

(Continued)

FOREIGN PATENT DOCUMENTS

DE   29 33 950   9/1981

*Primary Examiner*—Cam N. Nguyen
(74) *Attorney, Agent, or Firm*—Scully, Scott, Murphy & Presser, P.C.

(57) ABSTRACT

A carrier and a catalyst useful for the oxidation of ethylene to ethylene oxide which uses the carrier. The carrier is composed of an inert, refractory solid support such as alpha alumina and has a surface exhibiting a plurality of nanometer scale protrusions projecting outwardly from the surface, and has a catalytically effective amount of silver thereon.

21 Claims, 4 Drawing Sheets

U.S. PATENT DOCUMENTS

2005/0145377 A1* 7/2005 Thors et al. ............... 165/133
2005/0197249 A1* 9/2005 Creyghton et al. .......... 502/439
2006/0111455 A1* 5/2006 Klaver et al. ............... 518/716

* cited by examiner

NANOMETER SCALE RESTRUCTURING OF ALUMINA CARRIER SURFACE AND CATALYSTS FOR THE PRODUCTION OF ALKENE OXIDES

BACKGROUND OF THE INVENTION

1. Field of the Invention

The invention pertains to a carrier for a catalyst useful for the epoxidation of an olefin. More particularly, the invention pertains to a carrier, and a catalyst useful for the oxidation of ethylene to ethylene oxide which uses the carrier. The carrier comprises an inert, refractory solid support such as alpha alumina and has a surface exhibiting a plurality of nanometer scale protrusions projecting outwardly from the surface, and having a catalytically effective amount of silver thereon.

2. Description of the Related Art

Alumina is well known to be useful as a catalyst support for the epoxidation of an olefin. A particularly useful support is for a catalyst comprising silver which is employed in the oxidation of ethylene to ethylene oxide. Support materials are made by fusing high purity aluminum oxide with or without silica. For this purpose the support material often comprises 90 percent or more by weight alpha alumina and 1 to 6 percent by weight silica. They may be very porous or non-porous and have a high or low surface area depending upon the use to be made of them. The support may contain any porous, inert material which does not detrimentally influence the catalytic reaction where it is used.

In the process of making a support, high-purity aluminum oxide, preferably alpha alumina, is thoroughly mixed with temporary and permanent binders. The temporary binders are thermally decomposable organic compounds of moderate to high molecular weight which, on decomposition, produce the desired pore structure of the support. The permanent binders are inorganic clay-type materials having fusion temperatures below that of the alumina and impart mechanical strength to the finished support. After thorough dry-mixing, sufficient water or other solvent is added to the mass to form the mass into a paste-like substance. The catalyst support particles are then formed from the paste by conventional means such as, for example, high pressure extrusion, granulation or other ceramic forming processes. The particles are then dried and are subsequently fired at an elevated temperature.

In the firing step, the temporary binders are thermally decomposed to carbon dioxide and water and are volatilized, leaving voids in the support mass. These voids are the genesis of the pore structure of the finished support. The catalyst support is then cooled, and during cooling the permanent binder sets, acting to bond the support particles, and thereby impart mechanical strength to the support and ensure maintenance of the pore structure.

Catalyst supports of desired characteristics can be readily produced by the foregoing procedure. Pore size, pore distribution and porosity are readily controlled by appropriate adjustment of the size of the starting alumina particles, and of the particle size and concentration of the temporary and of the permanent binders in the mixture. The larger the starting alumina particle size, the greater will be the porosity of the finished catalyst. The more homogenous in size are the alumina particles, the more uniform will be the pore structure. Similarly, increasing the concentration of the temporary binder will also increase the overall porosity of the finished catalyst support.

U.S. patents which describe the making of alumina supports include U.S. Pat. Nos. 2,499,675; 2,950,169 and 3,172,866. Other patents such as U.S. Pat. Nos. 3,222,129; 3,223,483 and 3,226,191 show the preparation of active aluminas. Methods of making highly porous aluminas are disclosed in U.S. Pat. Nos. 3,804,781; 3,856,708; 3,907,512 and 3,907,982. Alumina carriers having high thermal stability are disclosed in U.S. Pat. No. 3,928,236. Other more recent improvements in making catalyst carriers are discussed in U.S. Pat. Nos. 3,987,155; 3,997,476; 4,001,144; 4,022,715; 4,039,481; 4,098,874 and 4,242,233.

The use of alkali metals and transition metals as a promoter for silver catalysts employed in the production of ethylene oxide by the partial oxidation of ethylene in the vapor phase is well known. Such are disclosed in U.S. Pat. Nos. 4,010,155; 4,012,425; 4,123,385; 4,066,575; 4,039,561 and 4,350,616. These promoters are used in conjunction with the silver coating on the surfaces of the support.

One of the problems with catalysts of the above type is that they have insufficient activity and stability under conditions of use. It would therefore be desirable to improve the catalytic activity and stability of the catalysts. It has been unexpectedly found that by modifying the surface topography of the catalyst carrier, by providing the carrier surface with nanometer size surface protrusions, that a significant improvement in catalyst performance is achieved. The catalysts are more active and stable compared to similar catalysts prepared with supports not having such protrusions.

SUMMARY OF THE INVENTION

The invention provides a carrier for a catalyst useful for the epoxidation of an olefin which comprises an inert, refractory solid support, the support having a surface and a plurality of protrusions projecting outwardly from the surface of the support, which protrusions are present at a frequencies in a range of from about 250 cycles/micrometer or more.

The invention also provides a process for producing a carrier for a catalyst useful for the epoxidation of an olefin which comprises providing an inert, refractory solid support, the support having a surface, and treating a surface of the support to thereby provide a plurality of protrusions projecting outwardly from the surface of the support, which protrusions are present at a frequencies in a range of from about 250 cycles/micrometer or more.

The invention further provides a catalyst useful for the epoxidation of an olefin which comprises a carrier which comprises an inert, refractory solid support, the support having a surface and a plurality of protrusions projecting outwardly from the surface, which protrusions are present at a frequencies in a range of from about 250 cycles/micrometer or more; the carrier comprising a catalytically effective amount of silver thereon.

The invention still further provides a process for the oxidation of ethylene to ethylene oxide which comprises the vapor phase oxidation of ethylene with molecular oxygen in a fixed bed, tubular reactor, in the presence of the above catalyst.

DETAILED DESCRIPTION OF THE INVENTION

Figure 1:
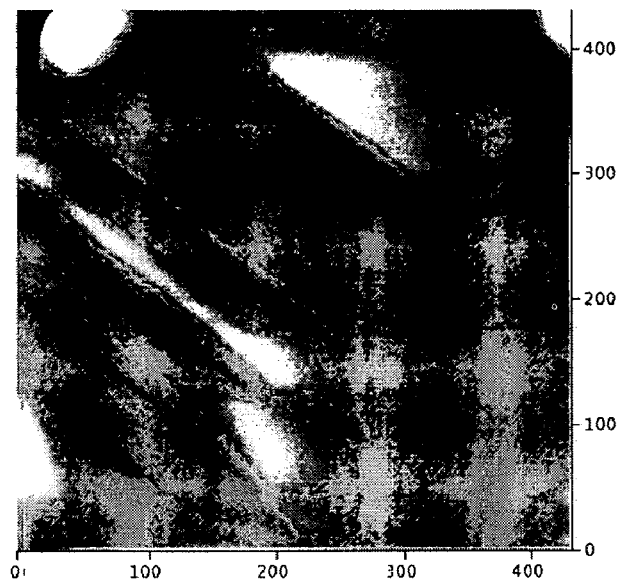
FIG. 1 is an atomic force microscope top view image of the surface of carrier A.

In the preparation of the inventive a carrier, one begins with an inert, solid, refractory support as is well known in the art and generally commercially available. The support has a surface which is treated according to the invention to provide a plurality of nanoscale protrusions projecting outwardly from the support surface.

The support employed in this invention may be selected from a large number of inert, solid, refractory supports which may be porous or non-porous. They are relatively inert to the epoxidation feedstock materials, products and reaction conditions for the intended use, such as for the epoxidation of an olefin, for example the oxidation of ethylene to ethylene oxide by the vapor phase oxidation of ethylene with molecular oxygen. The support may comprise aluminum oxide such as alpha-alumina, charcoal, pumice, magnesia, zirconia, titania, kieselguhr, fuller's earth, silicon carbide, silica, silicon carbide, silicon dioxide, clays, artificial zeolites, natural zeolites, ceramics and combination thereof. The preferred carriers are alpha-alumina particles which are often bonded together by a bonding agent and have a very high purity, i.e., about 95% or more, preferably 98 wt. % or more alpha-alumina. Remaining components may be other phases of alumina, silica, alkali metal oxides (e.g., sodium oxide) and trace amounts of other metal-containing and/or non-metal-containing additives or impurities. A wide variety of such carriers are commercially available. Suitable alumina carriers are manufactured and generally commercially available from United Catalysts, Inc., of Louisville, Ky., and the Norton Company, of Akron, Ohio.

Certain types of alpha alumina-containing supports are particularly preferred. These alpha alumina supports have relatively uniform pore diameters and are more fully characterized by having a B.E.T. surface area of from about 0.03 $m^2/g$ to about 10 $m^2/g$, preferably from about 0.05 $m^2/g$ to about 5 $m^2/g$, more preferably from about 0.1 $m^2/g$ to about 3 $m^2/g$; and water pore volumes of from about 0.10 cc/g to about 0.85 cc/g, preferably from about 0.25 cc/g to about 0.75 cc/g. Median pore diameters for these supports range from about 0.5 micrometers to about 50 micrometers. The supports may have monomodal, bimodal or multimodal pore distributions. The surface acidity of the support, as determined by irreversible ammonia sorption at 100° C., is often less than about 2 micromoles per gram of support, preferably less than about 1.5 micromoles per gram of support, and often from about 0.05 to 1.0 about micromoles per gram of support. Processes for making supports are described, for instance in U.S. Pat. Nos. 4,575,494; 3,172,866; 4,356,113; 4,082,697; 4,001,144; 3,856,708; 3,850,849 and 3,526,602, all herein incorporated by reference. Regardless of the character of the support used, it is usually shaped into particles, chunks, pieces, pellets, rings, spheres, wagon wheels, cross-partitioned hollow cylinders, and the like, of a size suitable for employment in fixed bed reactors. Desirably, the support particles may have "equivalent diameters" in the range of from about 3 mm to about 10 mm and preferably in the range of from about 4 mm to about 8 mm, which are usually compatible with the internal diameter of the tube reactors in which the catalyst is placed. "Equivalent diameter" is the diameter of a sphere having the same external surface (i.e. neglecting surface within the pores of the particle) to volume ratio as the support particles being employed.

In general, a suitable catalyst support of the present invention can be prepared by mixing the refractory material, such as alumina, a solvent such as water, a temporary binder or burnout material, a permanent binder and/or a porosity controlling agent. Temporary binders, or burnout materials, include cellulose, substituted celluloses, e.g. methylcellulose, ethylcellulose, and carboxyethylcellulose, stearates, such as organic stearate esters, e.g. methyl or ethyl stearate, waxes, granulated polyolefins, particularly polyethylene and polypropylene, walnut shell flour, and the like which are decomposable at the temperatures employed. These are responsible for producing the porosity of the support material. Burnout material is used primarily to ensure the preservation of a porous structure during the green, or unfired phase in which the mixture may be shaped into particles by molding or extrusion processes. It is essentially totally removed during the firing to produce the finished support. The supports of the invention are preferably made with the inclusion of a bond material such as silica with an alkali metal compound in sufficient amount to substantially prevent the formation of crystalline silica compounds. Permanent binders, include inorganic clay-type materials. A convenient binder material which may be incorporated with the alumina particles is a mixture of boehmite, an ammonia stabilized silica sol and a soluble sodium salt. The formed paste is extruded or molded into the desired shape and fired at a temperature of from about 1200° C. to about 1600° C. to form the support. Where the particles are formed by extrusion it may be desirable to include conventional extrusion aids. The amounts of the components to be used are to some extent interdependent and will depend on a number of factors that relate to the equipment used. However these matters are well within the general knowledge of a person skilled in the art of extruding ceramic materials. The performance of the support is enhanced if it is washed to remove soluble residues.

The inert, solid, refractory support is then treated according to the invention, to provide it with a surface topography having a plurality of protrusions projecting outwardly from the surface. The surface topography is provided by a treatment effective to partially dissolve the surface of the support and forming nanometer size protrusions by re-deposition of a fraction of the dissolved material back onto the surface in the form of features having the shape of rods, tubes, fibers or combinations thereof. The protrusions may be formed by soaking the support in a solution of an organic acid, an inorganic acid, a base, a salt, or combinations thereof for a time and at temperature sufficient to dissolve a portion of the support and redeposit the dissolved portion back onto the surface of the support. A useful treatment is conducted by soaking the support in a solution of an alkali hydroxide such as sodium hydroxide, potassium hydroxide, or an acid such as $HNO_3$. In one embodiment, the treating is conducted by soaking the support in an aqueous solution of an alkali hydroxide, or $HNO_3$ at a concentration in the range of from about 0.01 molar to about 10 molar, preferably from about 0.05 molar to about 5 molar, and still more preferably from about 0.1 molar to about 3 molar. Useful soaking times may range from about 1 minute to about 30 days, preferably from about 1 minute to about 5 days, more preferably from about 1 minute to about 1 day. Useful solution temperatures may range from about 0° C. to about 250° C., preferably from about 10° C. to about 200° C., and more preferably from about 20° C. to about 150° C. After soaking, the support can be optionally dried by heating at from about 80° C. to about 500° C., preferably from about 90° C. to about 300° C., more preferably from about 100° C.

to about 200° C. Soaking can be done at static conditions or with solution circulation. The treatment optionally may include soaking at one temperature, usually higher, followed by soaking at different temperature, usually lower. Optionally, soaking can be done in presence of a templating reagent in the treatment solution. The templating reagent may be used to control the size and uniformity of the protrusions. Suitable templating reagents non-exclusively include alkylamines, diaminoalkanes, aromatic amines, tetra-alkylammonium hydroxide and halides, cholesterol and polypeptides from nature, organic acids and their salts. When a templating reagent is used it may be used in the treating solution in an amount of from about 0.01 M to about 5 M, preferably from about 0.05 M to about 3 M and more preferably from about 0.1 M to about 1 M. After soaking the support is preferably washed, such as with water, to remove unreacted dissolved material and treating solution and optionally dried.

The surface can be characterized by detecting protrusions using an AFM (atomic force microscope) or SEM (scanning electron microscope), and/or by measuring a topography change of the support surface. The protrusions have an average diameter in the range of from about 1 nm to about 100 nm, preferably from about 5 nm to about 50 nm and more preferably from about 10 nm to about 30 nm. The protrusions have an average height in the range of from about 1 nm to about 300 nm, more preferably from about 5 nm to about 200 nm, still more preferably from about 10 nm to about 100 nm. It has been found that more active and stable catalysts are produced when the surface topography is modified to provide a surface feature frequencies in a range of from about 250 cycles/micrometer or more, preferably from about 250 to 800 cycles/micrometer, and more preferably from about 250 to about 500 cycles/micrometer as measured by power spectral density analysis of surface AFM images.

In order to produce a catalyst for the oxidation of ethylene to ethylene oxide, a carrier having the above characteristics is then provided with a catalytically effective amount of silver thereon. The catalysts are prepared by impregnating the treated supports with silver ions, compounds, complexes and/or salts dissolved in a suitable solvent sufficient to cause deposition of silver precursor compound onto the support. The impregnated carrier is then removed from the solution and the deposited silver compound is reduced to metallic silver by high temperature calcination. Also preferably deposited on the support either prior to, coincidentally with, or subsequent to the deposition of the silver are suitable promoters in the form of ions, compounds and/or salts of an alkali metal dissolved in a suitable solvent. Also deposited on the carrier either prior to, coincidentally with, or subsequent to the deposition of the silver and/or alkali metal are suitable transition metal ions, compounds, complexes and/or salts dissolved in an appropriate solvent.

The treated supports as described above is impregnated with a silver impregnating solution, preferably an aqueous silver solution. The support is also impregnated at the same time or in a separate step with various catalyst promoters. Preferred catalysts prepared in accordance with this invention contain up to about 45% by weight of silver, expressed as metal, deposited upon the surface and throughout the pores of a porous refractory support. Silver contents, expressed as metal, of from about 1 to about 40% based on weight of total catalyst are preferred, while silver contents of from about 8 to about 35% are more preferred. The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide and selectivity and activity stability within catalyst life. Useful silver containing compounds non-exclusively include silver oxalate, silver nitrate, silver oxide, silver carbonate, a silver carboxylate, silver citrate, silver phthalate, silver lactate, silver propionate, silver butyrate and higher fatty acid salts and combinations thereof.

This catalyst comprises a catalytically effective amount of silver, a promoting amount of alkali metal, a promoting amount of a transition metal supported on a porous, refractory support. As used herein the term "promoting amount" of a certain component of a catalyst refers to an amount of that component that works effectively to provide an improvement in one or more of the catalytic properties of that catalyst when compared to a catalyst not containing said component. The exact concentrations employed, of course, will depend upon, among other factors, the desired silver content, the nature of the support, the viscosity of the liquid, and solubility of the silver compound.

In addition to silver, the catalyst also contains an alkali metal promoter selected from lithium, sodium, potassium, rubidium, cesium or combinations thereof, with, cesium being preferred. The amount of alkali metal deposited on the support or catalyst or present on the support or catalyst is to be a promoting amount. Preferably the amount will range from about 10 ppm to about 3000 ppm, more preferably from about 15 ppm to about 2000 ppm and even more preferably from about 20 ppm to about 1500 ppm and yet even more preferably from about 50 ppm to about 1000 ppm by weight of the total catalyst, measured as the metal.

The catalyst also preferably contains a transition metal promoter which comprises an element from Groups 5b, 6b, 7b and 8 of the Periodic Table of the Elements, and combinations thereof. Preferably the transition metal comprises an element selected from Group 7b of the Periodic Table of the Elements. More preferred transition metals are rhenium, molybdenum, and tungsten, with molybdenum and rhenium most preferred. The amount of transition metal promoter deposited on the support or catalyst or present on the support or catalyst is to be a promoting amount. The transition metal promoter may be present in an amount of from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprising a promoting amount of one or more sulfur components, one or more fluorine containing components, or combinations thereof.

The silver solution used to impregnate the support is may also comprise an optional solvent or complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount of from about 0.1 to about 5.0 moles of ethylene diamine per mole of silver, preferably from about 0.2 to about 4.0 moles, and more preferably from about 0.3 to about 3.0 moles of ethylene diamine for each mole of silver.

When a solvent is used it may be water-based, or organic-based, and may be polar or substantially or totally non-polar. In general, the solvent should have sufficient solvating power to solubilize the solution components. At the same time, it is preferred that the solvent be chosen to avoid having an undue influence on or interaction with the solvated promoters. Examples of organic-based solvents include, but are not limited to, alcohols, in particular alkanols; glycols, in particular alkyl glycols; ketones; aldehydes; amines; tetrahydrofuran; nitrobenzene; nitrotoluene; glymes, in particular glyme, diglyme and tetraglyme; and the like. Organic-based solvents which have 1 to about 8 carbon atoms per molecule are preferred. Mixtures of organic solvents, or of water and one or more organic solvents may be used, provided that such mixed solvents function as desired herein The concentration of silver salt in the solution is in the range of from about 0.1% by weight to the maximum permitted by the solubility of the particular salt/solubilizing agent combination employed. It is generally very suitable to employ silver salts solutions containing from 0.5% to about 45% by weight of silver with silver salt concentrations of from 5 to 30% by weight being preferred.

Impregnation of the selected support is achieved in conventional manners by excess solution impregnation, incipient wetness, etc. Typically support material is placed in the silver solution until a sufficient amount of the solution is absorbed by the support. Preferably the quantity of the silver solution used to impregnate the porous support is no more than is necessary to fill the pore volume of the support. The silver containing liquid penetrates by absorption, capillary action and/or vacuum into the pores of the support. A single impregnation or a series of impregnations, with or without intermediate drying, may be used, depending in part on the concentration of the silver salt in the solution. Impregnation procedures are described in U.S. Pat. Nos. 4,761,394, 4,766, 105, 4,908,343, 5,057,481, 5,187,140, 5,102,848, 5,011,807, 5,099,041 and 5,407,888, which are incorporated herein by reference. Known prior procedures of pre-deposition, co-deposition and post-deposition of various the promoters can be employed.

Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to optimize conditions and results by taking into account feedstock costs, energy costs, by-product removal costs and the like. The particular combination of silver, support, alkali metal promoter, and transition metal promoter of the instant invention will provide an improvement in one or more catalytic properties over the same combination of silver and support and none, or only one promoter.

After impregnation, the support impregnated with silver precursor compound and the promoters is calcined or activated, for a time sufficient to reduce the silver component to metallic silver and to remove volatile decomposition products from the silver containing support. The calcination is accomplished by heating the impregnated support, preferably at a gradual rate, to a temperature in the range of from about 200° C. to about 600° C., preferably from about 250° C. to about 500° C., and more preferably from about 300° C. to about 450° C., at a reaction pressures in the range of from 0.5 to 35 bar, for a time sufficient to convert the contained silver to silver metal and to decompose all or substantially all of present organic materials and remove the same as volatiles. In general, the higher the temperature, the shorter the required reduction period. A wide range of heating periods have been suggested in the art to thermally treat the impregnated support, (e.g., U.S. Pat. No. 3,563,914 suggests heating for less than 300 seconds, U.S. Pat. No. 3,702,259 discloses heating from 2 to 8 hours at a temperature of from 100° C. to 375° C. to reduce the silver salt in the catalyst; usually for from about 0.5 to about 8 hours, however, it is only important that the reduction time be correlated with temperature such that substantially complete reduction of silver salt to catalytically active metal is accomplished. A continuous or step-wise heating program may be used for this purpose.

The impregnated support is maintained under an atmosphere comprising a combination of an inert gas and from about 10 ppm to about 5% by volume of a gas of an oxygen containing oxidizing component. For purposes of this invention, inert gases are defined as those which do not substantially react with the catalyst preparation components under the catalyst preparation conditions chosen. These include nitrogen, argon, krypton, helium, and combinations thereof, with the preferred inert gas being nitrogen. The gas of an oxygen containing oxidizing component may include molecular oxygen, $CO_2$, $NO$, $NO_2$, $N_2O_3$, $N_2O_4$, or $N_2O_5$, or a substance capable of forming $NO$, $NO_2$, $N_2O_3$, $N_2O_4$, or $N_2O_5$ under calcining conditions, or combinations thereof, and optionally comprising $SO_3$, $SO_2$, $P2O_5$, $P_2O_3$ or combinations thereof. Of these molecular oxygen is preferred and more preferred is a combination of $O_2$ with $NO$ or $NO_2$. In a useful embodiment, the atmosphere comprises from about 10 ppm to about 1% by volume of a gas of an oxygen containing oxidizing component. In another useful embodiment, the atmosphere comprises from about 50 ppm to about 500 ppm of a gas of an oxygen containing oxidizing component.

Ethylene Oxide Production

Generally, the commercially practiced ethylene oxide production processes are carried out by continuously contacting an oxygen containing gas with ethylene in the presence of the present catalysts at a temperature in the range of from about 180° C. to about 330° C. and preferably about 200° C. to about 325° C., more preferably from about 225° C. to about 270° C., at a pressure which may vary from about atmospheric pressure to about 30 atmospheres depending on the mass velocity and productivity desired. Pressures in the range of from about atmospheric to about 500 psi are generally employed. Higher pressures may, however, be employed within the scope of the invention. Residence times in large-scale reactors are generally on the order of about 0.1-5 seconds. Oxygen may be supplied to the reaction in an oxygen containing stream, such as air or as commercial oxygen. The resulting ethylene oxide is separated and recovered from the reaction products using conventional methods. However, for this invention, the ethylene oxide process envisions the normal gas recycle encompassing carbon dioxide recycle in the normal concentrations, e.g., about 0.5 to 6 volume percent. A usual process for the oxidation of ethylene to ethylene oxide comprises the vapor phase oxidation of ethylene with molecular oxygen in the presence of the inventive catalyst in a fixed bed, tubular reactor. Conventional commercial fixed bed ethylene oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst.

The inventive catalysts have been shown to be particularly selective catalysts in the oxidation of ethylene with molecular oxygen to ethylene oxide. The conditions for carrying out such an oxidation reaction in the presence of the catalysts of the present invention broadly comprise those described in the prior art. This applies, for example, to suitable temperatures, pressures, residence times, diluent materials such as nitrogen, carbon dioxide, steam, argon, methane or other saturated hydrocarbons, the presence or absence of moderating agents to control the catalytic action, for example, 1,2-dichloroethane, vinyl chloride or chlorinated polyphenyl compounds, the desirability of employing recycle operations or applying successive conversion in different reactors to increase the yields of ethylene oxide, and any other special conditions which may be selected in processes for preparing ethylene oxide. Molecular oxygen employed as a reactant may be obtained from conventional sources. The suitable oxygen charge may be relatively pure oxygen, a concentrated oxygen stream comprising oxygen in major amount with lesser amounts of one or more diluents such as nitrogen, argon, etc., or another oxygen containing stream such as air. The use of the present catalysts in ethylene oxidation reactions is in no way limited to the use of specific conditions among those which are known to be effective.

The resulting ethylene oxide is separated and recovered from the reaction products by conventional methods known and used in the art. Use of the silver catalysts of the invention in ethylene oxide production processes gives higher overall ethylene oxidation selectivities to ethylene oxide at a given ethylene conversion than are possible with conventional catalysts.

In the production of ethylene oxide, reactant feed mixtures may contain 0.5 to 45% ethylene and 3 to 15% oxygen, with the balance comprising comparatively inert materials including such substances as nitrogen, carbon dioxide, methane, ethane, argon and the like. In a preferred application of the silver catalysts of the invention ethylene oxide is produced when an oxygen containing gas of about 95% or more of oxygen. Only a portion of the ethylene usually is reacted per pass over the catalyst and after separation of the desired ethylene oxide product and the removal of appropriate purge stream and carbon dioxide to prevent uncontrolled build up of inerts and/or by-products, unreacted materials are returned to the oxidation reactor. For purposes of illustration only, the following are conditions that are often used in current commercial ethylene oxide reactor units. GHSV—1500-10,000; Inlet pressure—150-400 psig; Inlet Feed: ethylene 1-40%; $O_2$—3-12%; $CO_2$—2-40%; ethane 0-3%; argon and/or methane and/or nitrogen: 0.3-20 ppmv total diluent chlorohydrocarbon moderator; coolant temperature—180-315° C.; catalyst temperature 180° C.; $O_2$ conversion level—10-60%; EO Production (Work Rate) 2-16 lbs. EO/cu.ft. catalyst/hr.

In other descriptions of processes of ethylene oxide production addition of oxygen-containing gases to the feed increased the efficiency. For example in U.S. Pat. No. 5,112,795 5 ppm of nitric oxide was added to the gas feed of composition: 8 volume % oxygen, 30 volume % ethylene, about 5 ppmw ethyl chloride and the balance nitrogen.

The following non-limiting example serves to illustrate the invention.

EXAMPLES

Carrier A (Comparative)

Carrier A was used untreated, as received from the manufacturer. Surface AFM imaging of this carrier is shown on FIG. 1. No visible protrusions on the surface are detected. Power spectral density analysis show no feature frequencies above 200 cycles/micrometer.

Carrier B (Comparative)

Carrier B was prepared by taking 600 g of Carrier A and washing it by circulating 780 g of a 0.015 M water solution of $NH_4F$. At the contact of liquid and carrier the temperature was raised from room temperature to 80° C. in 30 minutes. Washing continued for 3 hours at 80° C. after which the solution was drained. 780 g of deionized water at room temperature was used to rinse the carrier with circulation for 30 minutes, after which the water was drained and carrier dried overnight at 150° C.

Figure 2:
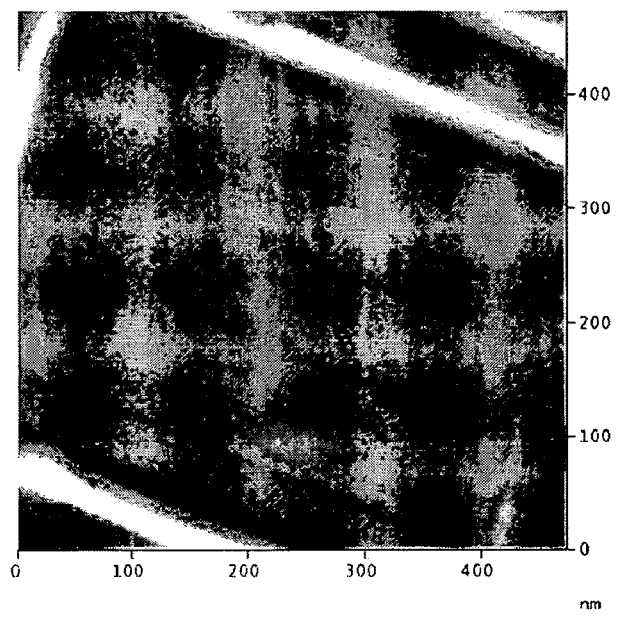
FIG. 2 is an atomic force microscope top view image of the surface of carrier B.

No visible protrusions are observed on the surface AFM image after treatment of the carrier, as seen in FIG. 2. Power spectral density analysis indicated the surface's feature frequencies are below 180 cycles/micrometer.

Carrier C

Carrier C, according to the invention, was obtained by taking 510 g of Carrier A and treating it with 663 g of a circulating 0.25 M NaOH water solution. At the contact of NaOH solution with the carrier, the temperature was raised from room temperature to 80° C. over 30 minutes and then kept at this temperature for 1 hour. After treatment, the solution was drained and 663 g of circulating deionized water at room temperature was used for rinsing the carrier for 1 hour, after which it was drained. The rinsing procedure was repeated 2 more times. The treated carrier was dried at 150° C. overnight.

Figure 3:
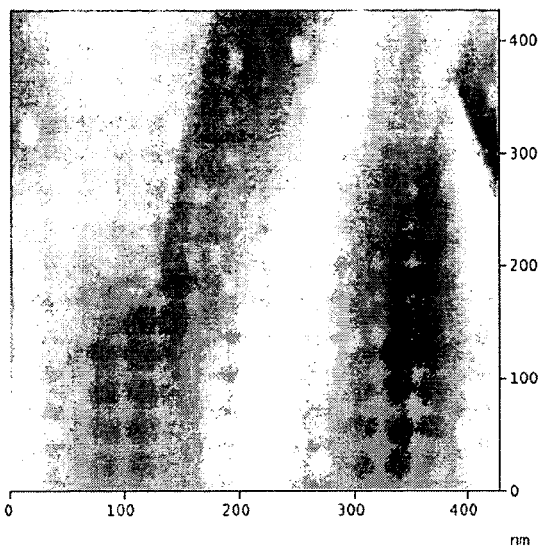
FIG. 3 is an atomic force microscope top view image of the surface of carrier C.

Surface AFM image clearly shows the formation of protrusions up to 10 nm in height, as seen in FIG. 3. Power spectral density analysis showed feature frequencies higher than 200 cycles/micron and as high as 430 cycles/micrometer.

Carrier D

Carrier D, according to the invention, was obtained by taking 940 g of Carrier A and treating it with 1222 g of a circulating 1.25 M NaOH water solution. At the contact of NaOH solution with the carrier the temperature was raised from room temperature to 80° C. over 30 minutes and then kept at this temperature for 1 hour. After treatment, the solution was drained and 1222 g of circulating deionized water at room temperature was used for rinsing of carrier for 1 hour after which it was drained. The rinsing procedure was repeated 4 more times. The treated carrier was dried at 150° C. overnight.

Figure 4:
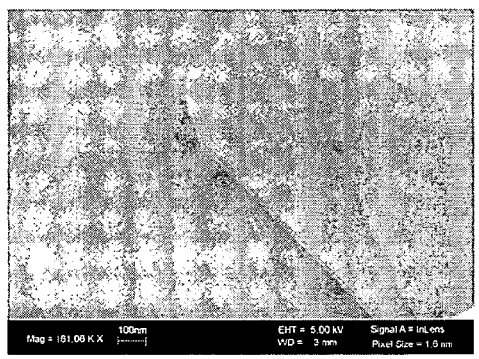
FIG. 4 is a surface scanning electron micrograph of the surface of carrier A shown as (a), and D shown as (b).
Figure 4:
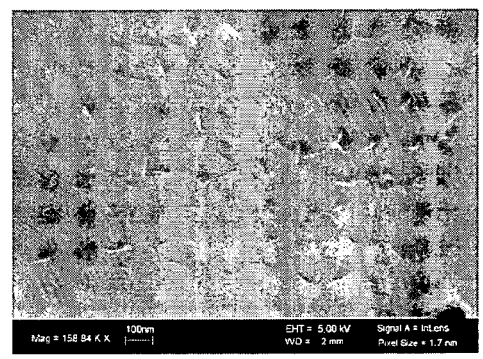

SEM images of the surface before treatment and after treatment are shown on FIG. 4. Formation of surface grain shape protrusions is evident after treatment.

Carrier E (Comparative)

Carrier E was another alpha-alumina carrier from same manufacturer. It had essentially the same physical properties as Carrier A, but a different chemical composition.

Carrier F (Comparative)

Carrier F was obtained by taking 600 g of Carrier E and treating it as in the preparation of Carrier B.

Carrier G

Carrier G, according to the invention, was obtained by placing 510 g of Carrier E in a plastic flask, evacuating the flask to below 10 Torr pressure, and introducing 663 g of 1 M $HNO_3$ into the flask. After the carrier was covered with liquid, the vacuum was broken and the carrier was covered with $HNO_3$ solution at room temperature for one hour.

After 1 hour, the $HNO_3$ solution was drained and 663 g of deionized water at room temperature was added to the carrier for rinsing. The carrier was rinsed for 30 minutes by occasional shaking of the flask. After 30 minutes the liquid was drained and another 663 g of deionized water at room temperature was added, used for 1 hour rinsing and drained. The last step was repeated one more time, after which the treated carrier was dried at 150° C. overnight.

Catalyst Preparation and Testing

1. Silver Stock Solution Preparation.

A silver solution was prepared using the following components (parts are by weight):
Silver oxide—834 parts
Oxalic acid—444 parts
Ethylene diamine—509 parts Silver oxide was mixed with water, at room temperature, followed by the gradual addition of the oxalic acid. The mixture was stirred for 15 minutes and at that point, the color of the black suspension of silver oxide changed to the gray/brown color of silver oxalate. The mixture was filtered and the solids were washed with 3 liters of de-ionized water. The sample was placed in an ice bath and stirred while ethylene diamine and water (as a 66%/34% mixture) were added slowly in order to maintain the reaction temperature lower than 33° C. After the addition of the ethylenediamine/water mixture, the solution was filtered at room temperature. The clear filtrate was utilized as a silver/amine stock solution for catalyst preparation.

2. Catalyst Preparation and Testing.

a. Promoter Addition:

The clear silver stock solution obtained above was diluted with a 66/34 mixture of ethylenediamine/water. In addition, cesium hydroxide was added to the solution in order to prepare a catalyst containing catalytically effective amounts of silver and cesium.

b. Catalyst Impregnation:

An 80 g to 100 g of carrier sample was placed in a pressure vessel and then exposed to vacuum until the pressure was below 50 mm Hg. 160 ml of the adjusted silver/promoter solution was introduced to the flask while it was still under vacuum. The pressure of the vessel was allowed to rise to atmospheric pressure. The catalyst was separated from the solution and was ready for calcination.

c. Catalyst Calcination:

Calcination, i.e. the deposition of silver, was induced by heating the catalyst up to the decomposition temperature of the silver salt. This was achieved via heating in a furnace that has several heating zones in a controlled atmosphere. The catalyst was loaded on a moving belt that entered the furnace at ambient temperature. The temperature was gradually increased as the catalyst passed from one zone to the next. It was increased, up to 400° C., as the catalyst passed through 4 heating zones. After the heating zones, the belt passed through a cooling zone that gradually cooled the catalyst to ambient temperature. The total residence time in the furnace was 42 minutes. The atmosphere in the furnace was controlled through the use of nitrogen flow in the heating zones.

d. Catalyst Testing:

The catalyst, 2 g, was tested in a heated stainless steel tube. A gas mixture containing 15% ethylene, 7% oxygen, and 78% inert, mainly nitrogen and carbon dioxide, was passed through the catalyst at 300 psig. The temperature of the reaction was adjusted to maintain catalyst at weight work rate (WWR)=737.

Silver catalysts promoted with cesium were prepared on carriers A, B, C, D, E, F and G. The catalysts contained a catalytically effective concentration of silver. Optimum cesium concentration was experimentally found by preparing catalysts with cesium varying from under 400 ppm to above 600 ppm. Best catalysts were compared in a test at weight Work Rate=737.

Example 1

Figure 5:
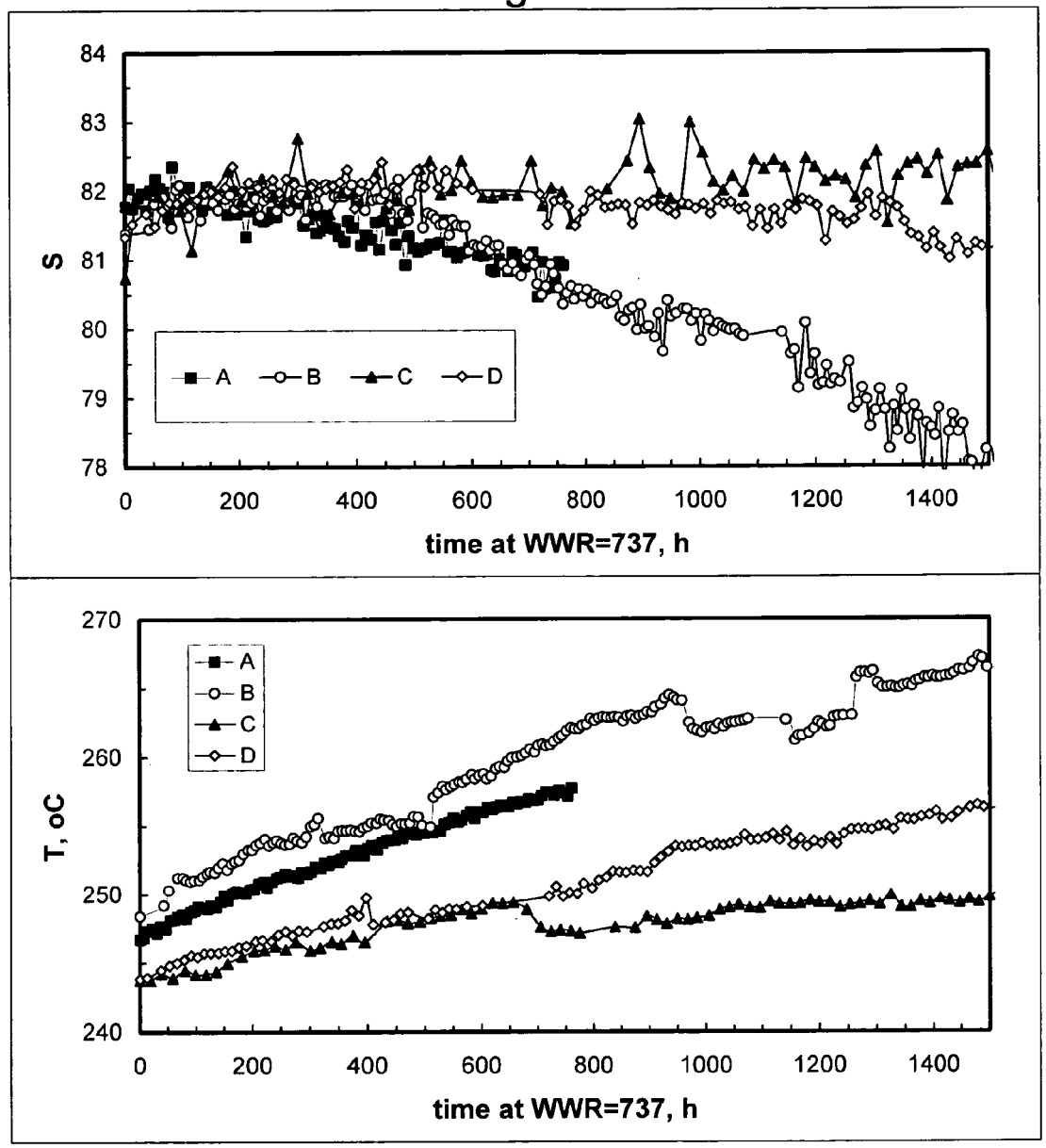
FIG. 5 is a graph of the performance of catalysts made on carriers A, B, C and D.

FIG. 5 shows selectivity and activity change over time for catalysts prepared on Carriers A, B, C and D. Catalysts made on carriers C and D with surface topography modified according to the invention are clearly more active and stable comparably to catalysts made on carriers A and B without such surface modifications.

Example 2

Figure 6:
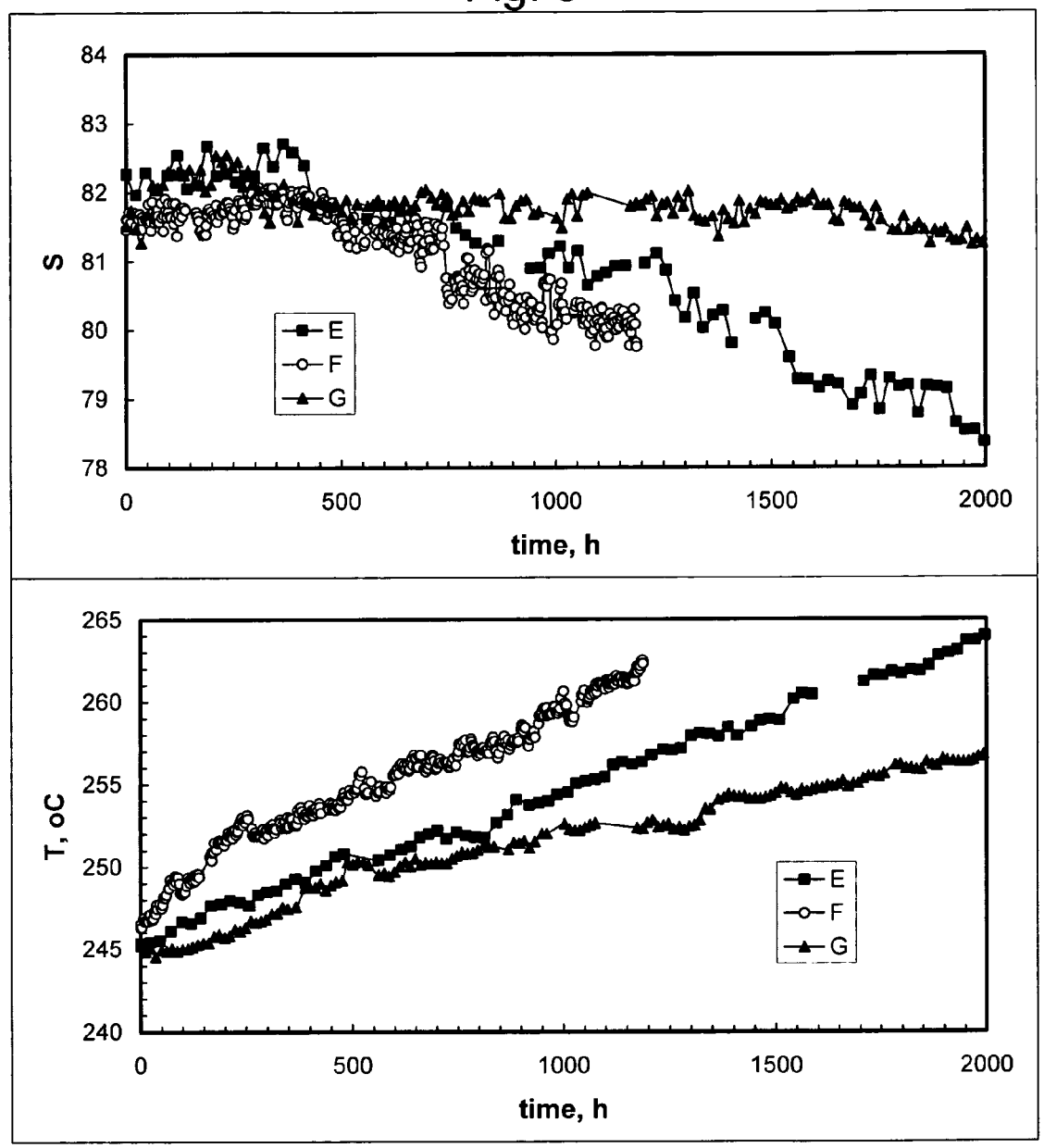
FIG. 6 is a graph of the performance of catalysts made on carriers E, F and G.

FIG. 6 shows selectivity and activity change over time for catalysts prepared on Carriers E, F and G. Catalysts on carriers with no treatment or after treatment non effective in modifying surface, as on carriers E and F, are less stable and less active than catalysts made on carrier G with surface modified by $NHO_3$ according to the invention.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A catalyst carrier useful for the epoxidation of an olefin which comprises an inert, refractory solid support, the support having a surface and a plurality of protrusions projecting outwardly from the surface of the support, which protrusions are present on the surface of the support at a frequency in a range of from about 250 cycles/micrometer or more.

2. The carrier of claim 1 wherein the support comprises aluminum oxide, charcoal, pumice, magnesia, zirconia, titania, kieselguhr, fuller's earth, silicon carbide, silica, silicon dioxide, magnesia, clays, artificial zeolites, natural zeolites, ceramics or combination thereof.

3. The carrier of claim 1 wherein the protrusions are in the shape of rods, tubes, fibers, or combinations thereof.

4. The carrier of claim 1 wherein the protrusions have an average diameter in the range of from about 1 nm to about 100 nm.

5. The carrier of claim 1 wherein the protrusions have an average height in the range of from about 1 nm to about 300 nm.

6. The carrier of claim 1 wherein the protrusions are present on the surface of the support at a frequency in the range from about 250 to about 800 cycles/micrometer as measured by power spectral density analysis.

7. A process for producing a catalyst carrier useful for the epoxidation of an olefin comprising providing an inert, refractory solid support, the support having a surface, and treating the surface of the support to provide a plurality of protrusions projecting outwardly from the surface of the support, which protrusions are present on the surface of the support at a frequency in a range of from about 250 cycles/micrometer or more.

8. The process of claim 7 wherein the protrusions are in the shape of rods, tubes, fibers, or combinations thereof.

9. The process of claim 7 wherein the protrusions have an average diameter in the range of from about 1 nm to about 100 nm.

10. The process of claim 7 wherein the protrusions have an average height in the range of from about 1 nm to 300 nm.

11. The process of claim 7 wherein the protrusions are present on the surface of the support at a frequency in the range from about 250 to about 800 cycles/micrometer as measured by power spectral density analysis.

12. The process of claim 7 wherein the treating is conducted by soaking the support in a solution of an organic acid, an inorganic acid, a base, a salt or combinations thereof for a time and at a temperature sufficient to dissolve a portion of the support, and redeposit the dissolved portion back onto the surface of the support.

13. The process of claim 7 wherein the treating is conducted by soaking the support in a solution of an alkali metal hydroxide or $HNO_3$.

14. The process of claim 7 wherein the treating is conducted by soaking the support in an aqueous solution of an alkali metal hydroxide or $HNO_3$ at a concentration in the range of from about 0.01 molar to about 10 molar.

15. The process of claim 7 wherein the treating is conducted by soaking the support in an aqueous solution of an alkali metal hydroxide or $HNO_3$ at a concentration in the range of from about 0.01 molar to about 10 molar for from about 1 minute to about 30 days and at a temperature of from about 0° C. to about 250° C., with optional subsequent drying.

16. A catalyst useful for the epoxidation of an olefin comprising; a catalyst carrier, which comprises an inert, refractory solid support, the support having a surface and a plurality of protrusions projecting outwardly from the surface, which protrusions are present on the surface of the support at a frequency in a range of from about 250 cycles/micrometer or more, and a catalytically effective amount of silver thereon.

17. The catalyst of claim 16 further comprising a promoting amount of a promoter supported thereon, wherein the promoter comprises one or more of an alkali metal containing compounds, one or more transition metal containing compounds, one or more sulfur components, one or more fluorine containing components, or combinations thereof.

18. The catalyst of claim 17 wherein the promoter is a transition metal containing compound comprising an element selected from the group consisting of Groups 5b, 6b, 7b and 8 of the Periodic Table of the Elements, and combinations thereof.

19. The catalyst of claim 18 wherein the transition metal containing compound comprises rhenium, molybdenum, tungsten or combinations thereof.

20. The catalyst of claim 17 wherein the promoter is an alkali metal containing compound comprising lithium, sodium, potassium, rubidium, cesium or combinations thereof.

21. A process for the oxidation of ethylene to ethylene oxide by vapor phase oxidation of ethylene with molecular oxygen in a fixed bed, tubular reactor, in the presence of the catalyst of claim 16.

* * * * *